United States Patent
Kuppuswamy et al.

(10) Patent No.: US 7,635,717 B2
(45) Date of Patent: Dec. 22, 2009

(54) PROCESS FOR THE PREPARATION OF AMINO METHYL CYCLO ALKANE ACETIC ACIDS

(75) Inventors: Nagarajan Kuppuswamy, Bangalore (IN); Sivaramakrishnan Hariharan, Bangalore (IN); Arulselvan Mariadas, Bangalore (IN)

(73) Assignee: Hikal Limited, Bangalore (IN)

( * ) Notice: Subject to any disclaimer, the term of this patent is extended or adjusted under 35 U.S.C. 154(b) by 0 days.

(21) Appl. No.: 10/535,253

(22) PCT Filed: Nov. 20, 2002

(86) PCT No.: PCT/IN02/00224

§ 371 (c)(1),
(2), (4) Date: Feb. 9, 2006

(87) PCT Pub. No.: WO2004/046085

PCT Pub. Date: Jan. 3, 2004

(65) Prior Publication Data

US 2006/0149099 A1 Jul. 6, 2006

(51) Int. Cl.
*A61K 31/195* (2006.01)
*C07C 229/32* (2006.01)

(52) U.S. Cl. .................................. 514/561; 562/507

(58) Field of Classification Search ............ None
See application file for complete search history.

(56) References Cited

U.S. PATENT DOCUMENTS

| 6,255,526 B1 | 7/2001 | Pesachovich et al. |
| 6,518,456 B1 * | 2/2003 | Peverali et al. ............. 562/507 |
| 2004/0068011 A1 * | 4/2004 | Cannata et al. ............. 514/561 |

FOREIGN PATENT DOCUMENTS

| WO | WO 98/28255 | 7/1998 |
| WO | WO 00/58268 | 10/2000 |
| WO | WO 02/44123 | 6/2002 |

OTHER PUBLICATIONS

Sigma-Aldrich #190764, 2-Propanol ACS Reagent 99.5%.*
Sigma-Aldrich #667390, Methanol solution.*
Sigma-Aldrich #179957, Methanol Laboratory Reagent 99.6%.*

* cited by examiner

*Primary Examiner*—Daniel M Sullivan
*Assistant Examiner*—Yevegeny Valenrod

(57) ABSTRACT

This invention relates to an improved process for the preparation of amino methyl cyclo alkane acetic acids. This invention particularly relates to an improved process for the preparation of gabapentin (which is chemically known as 1-aminomethyl-1-cyclohexaneacetic acid), which is a very well known agent useful for the treatment of epilepsy and other cerebral disorders. In the chemical series of 1-amino methyl cyclo alkane-1-acetic acids, Gabapentin, which is 1-amino methyl cyclo hexane-1-acetic acid has been developed as a drug having anti convulsive properties.

22 Claims, No Drawings

PROCESS FOR THE PREPARATION OF AMINO METHYL CYCLO ALKANE ACETIC ACIDS

BACKGROUND

This invention relates to an improved process for the preparation of amino methyl cyclo alkane acetic acids. This invention particularly relates to an improved process for the preparation of gabapentin (which is chemically known as 1-aminomethyl-1-cyclohexaneacetic acid), which is a very well known agent useful for the treatment of epilepsy and other cerebral disorders. In the chemical series of 1-amino methyl cyclo alkane-1-acetic acids, Gabapentin, which is 1-amino methyl cyclo hexane-1-acetic acid has been developed as a drug having anti convulsive properties.

Gabapentin has the formula I shown below

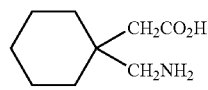

(I)

U.S. Pat. No. 4,024,175 & 4,087,544 and DE Pat. No 2460891 disclose this compound, process of its preparation and its uses.

The above patents describe various processes for the preparation of Gabapentin and similar compounds of the general formula 2 given below

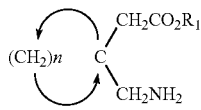

Wherein $R_1$ is a hydrogen atom or a lower alkyl radical and n is an integer with a value of 4 to 6 and their pharmaceutically acceptable salts.

The processes disclosed in these patents are based on known methods used for the preparation of primary amines. Specifically, they involve Curtius reaction of cycloalkane diacetic acid monoesters, Hoffmann reaction of cycloalkane diacetic acid monoamides or Lossen Rearrangement of 1-carboxymethylcycloalkane acetohydroxamic acid sulphonate esters.

In a variation of the Lossen Rearrangement, the process can be carried out on the O-sulphonyloxycycloalkane-1,1-diacetic (N-hydroxy)imide (U.S. Pat. No. 4,152,326, & Can patent no 1085420). These procedures go through an isocyanate or urethane that can be converted into the desired 1-aminomethyl-cycloalkane-1-acetic acid by acidic or basic hydrolysis. The aminoacid hydrochloride is isolated from the hydrolysate by evaporation of water.

In particular, in U.S. Pat. Nos. 4,024,175 and 4,087,544 and DE Pat. No. 2460891 monomethyl cyclohexane-1-acetic acid was transformed to the azide which was decomposed (Curtius reaction) in boiling toluene. The resultant isocyanate was hydrolysed with aqueous hydrochloric acid. The resultant solution was evaporated to dryness to give 1-aminomethylcyclohexane-1-acetic acid hydrochloride, which was converted to gabapentin with a basic ion-exchange resin.

In the same patents, 1,1-cyclopentane diacetic acid monoamide was treated with aqueous sodium hypobromite at −10 deg and the solution then heated at 60 deg for 2 hours. It was then acidified with 12 N hydrochloric acid and evaporated in vacuum. The residue was extracted with ethanol and the ethanol solution evaporated to give 1-amino methyl cyclopentane-1-acetic acid hydrochloride from which the free aminoacid was obtained by passage through a basic ion exchange resin.

In U.S. Pat. No. 4,152,326, N-(p-toluenesulphonyloxy)-1,1-cyclohexanediaceticacid imide was heated with 10% aqueous sodium hydroxide solution (Lossen Rearrangement) at 100 deg and the resultant solution acidified with concentrated hydrochloric acid and evaporated to dryness. The residue was digested with ethanol and filtered and the filtrate evaporated in vacuum to give gabapentin benzenesulphonate. Treatment of this material with the basic ion exchanger, IR-45, in the —OH form gave gabapentin.

In the ensuing years, there have been patents involving other routes which involve the hydrolysis of 2-azaspiro (4,5) decan-3-one of the formula 3, known conveniently as gabalactam, first isolated by Sircar (J. Ind. Chem. Soc., 1928, 5, 549; chem. Abstracts, 1929, 23, 818) with 1:1 hydrochlorid acid

(3)

(U.S. Pat. Nos. 5,091,567, 5,068,413, EP 414263 WO patent application no 9914184A1) to afford gabapentin as the hydrochloride salt.

Thus in U.S. Pat. No. 5,068,413 and EP patent no 414263, A2, gabalactam is mixed with 1:1 hydrochloric acid and boiled under reflux at 108 degree C. for 6 hrs, cooled and diluted with water. The mixture is extracted with methylene chloride to remove un-dissolved lactam. The aqueous solution is evaporated to dryness in vacuum and the residue washed with acetone to give gabapentin hydrochloride as the insoluble part.

In U.S. Pat. No. 5,091,567, gabalactam is similarly hydrolysed with hydrochloric acid to give gabapentin hydrochloride.

In WO patent application no 9914184A1, the lactam of the formula 3 is hydrolyzed with a mixture of 6N hydrochloric acid and dioxane at reflux for 4 hours. The solution is evaporated to dryness and the residue crystallized from methanol-ethyl acetate-heptane to afford gabapentin hydrochloride.

In two other patents (U.S. Pat. Nos. 4,956,473 & 4,958,644), the lactam of the formula 3 having an extra carbethoxy groups has been synthesized and hydrolyzed with 1:1 hydrochloric acid with concomitant removal of the carbethoxy group to afford gabapentin hydrochloride.

In U.S. Pat. No. 4,958,044, a solution of (1-cyano cyclohexyl) malonic acid dimethyl ester in ethanol was hydrogenated at 10 bars of hydrogen pressure and 90 deg C. on 3 g Raney Nickel for 4.5 hours. The solution was filtered and the filtrate evaporated to give 2-aza-(4-methoxy-carbonyl)spiro (4,5) decan-3-one (carbethoxy gaba lactam). This was mixed with 20% hydrochloric acid and stirred under reflux for 24 hours. The solution was evaporated to dryness and the residue worked up to give gabapentin hydrochloride.

Other methods to synthesize gabapentin directly without the intervention of gabalactam or gabapentin hydrochloride have also been described. In U.S. Pat. Nos. 5,095,148, 5,135, 455, 5,136,091, 5,149,870 & Can patent no 203017, (1-cyano cyclohexyl) acetic acid benzyl ester was hydrogenated in methanol using 5% Rhodium on carbon catalyst at 10 bars of hydrogen pressure for 23 hours at room temperature. Filtration of the mixture, concentrating the filtrate and diluting with ethanol gave a 27% yield of gabapentin.

In U.S. Pat. Nos. 5,132,451, 5,319,135 & 6,294,690, 1-cyanocyclohexane acetic acid was hydrogenated in methanol at room temperature for 2 hours, using 15% Rhodium on carbon catalyst containing 1% palladium. The mixture was filtered and the filtrate concentrated. Addition of isopropanol and stirring at 0-5 deg for 24 hrs gave gabapentin. In EP Patent no 414262B1,1-cyano cyclohexene acetic acid was hydrogenated on Raney nickel to produce Gabapentin.

In U.S. Pat. No. 6,294,690, benzo nitrile was subjected to a Birch reduction with lithium and liquid ammonia and the reduction intermediates trapped with ethyl bromo acetate. The resultant product was hydrolysed to (1-cyano cyclo hexa-2,5-dienyl) acetic acid which was hydrogenated in methanolic ammonium hydroxide for 3.5 hrs at 50 deg C. and 50 psi hydrogen pressure and on 5% palladium charcoal catalyst. The mixture was filtered and the filtrate concentrated to give crude gabapentin.

WO application No 2000039074 describes synthesis of gabapentin by hydrogenation of 1-nitromethylcyclohexyl acetic acid benzyl or diphenylmethyl ester.

By far the most widely used procedure for the preparation of gabapentin appears to be the removal of HCl from its hydrochloride salt. This has been accomplished in various ways, all of which except for four processes use a basic ion exchange resin (U.S. Pat. Nos. 4,024,175, 4,894,476, 4,960,931 & 6,054,482; Canada patent no 1085420; EP patent no 340677, 414263, WO patent application Nos 9914184 & 0001660) wherein the hydrochloride was mostly dissolved in water or some times in water and an alcohol.

In U.S. Pat. No. 4,024,175, gabapentin was obtained from its hydrochloride by treatment with a basic ion exchanger and crystallization from ethanol-ether. No experimental details are given in this patent.

In U.S. Pat. Nos. 4,894,476, 4,960,931 & 6,054,482, EP patent no 340677 a solution of gabapentin hydrochloride in de ionized water was poured into a column of Amberlite IRA-68 in the OH form and the column eluted with de ionized water. The eluate was concentrated on a rotovap at about 29-31 degree C. in vacuum to slurry. The slurry was mixed with isopropanol and cooled to give gabapentin monohydrate.

In Canadian Patent no 1085420, gabapentin benzene sulphonate salt was converted to gabapentin by exchange on Amberlite IR 45.

In EP Patent no 414263, gabapentin hydrochloride was converted to gabapentin by de ionising with the ion exchange resin IRA 68.

In WO 0001660, a solution of gabapentin hydrochloride in water was passed over ReliteEXA10 resin and the eluate was concentrated under vacuum. The concentrate was treated with 2-methoxy ethanol and a mixture of water and 2-methoxy ethanol was distilled out. Isopropanol was added to the resultant suspension; the mixture was heated to 60 deg C. for 30 minutes and cooled. After 2 hours at −5 to −10 deg C., the precipitate was filtered to give gabapentin.

Among the exceptions, in one case de-ionisation has been carried out in methanol. Thus in EP Patent no 1174418A 1 and WO 200064857, deionisation of a solution of gabapentin hydrochloride in methanol was achieved by passing through a weakly basic ion exchange resin BAYER MP-2. The methanolic eluate was concentrated by low-pressure distillation below 30 deg C. to give a dense suspension which was dissolved in methanol-water at 65 deg C. cooled and treated with isopropanol to give pharmaceutical grade gabapentin.

In another process reported in WO patent application no 00/58268, an aqueous solution of gabapentin hydrochloride was neutralized with 1 M NaOH to a pH of 7.14 and subjected to diafiltration at about 22 deg C., using a nano filtration multiplayer composite membrane having high selectivity for organic compounds with molecular weight higher than 150 and low selectivity to inorganic mono valent ions. The resultant solution is concentrated under reduced pressure below 35 deg C. and gabapentin is precipitated by isopropanol and crystallized from methanol.

In another process described in U.S. Pat. No. 6,255,526 B1, gabapentin hydrochloride was suspended in ethyl acetate and stirred with tri-n-butylamine at 25 deg C. for 2 hours. The precipitated gabapentin was collected by filtration and stirred with methanol at 25 deg C. for 14 hours and filtered off.

In another process presented in WO patent application no 02/34709-gabapentin hydrochlorides, obtained as a solution in n-butanol was poured over strong cationic resin (IMAC HP 1/10). After washing the column with water, gabapentin was eluted with aqueous ammonia. The ammonium solution was evaporated below 40 deg to a thick residue, which was heated with methanol and then stirred with isopropanol. The mixture was filtered to give gabapentin.

It can be seen from the above prior art literature; the process for the preparation of gabapentin is to access gabapentin hydrochloride by a suitable method and then subjecting it to ion exchange treatment. This process leads to the formation of gabapentin, mostly an aqueous solution, which is then evaporated. This process has to be conducted at a low temperature of 25 to 40 deg C. and a high vacuum in the range of 1 to 2 torr as otherwise lactamisation results leading to contamination of the resulting product. Water, having a low vapour pressure, the process of evaporation will be tedious and time consuming. In addition the use of a high vacuum for such long lengths of time will consume much energy. Hence the process becomes cost-inefficient and user un-friendly and therefore may not be suitable for industrial applications.

U.S. Pat. No. 6,054,482 claims that only by using the ion exchange method, gabapentin hydrochloride will give the pure aminoacid with less than 0.5% of residual gabalactam and 20 ppm of chloride. Above these levels, the storage stability of gabapentin is adversely affected, with build up of toxic gabalactam to undesirable levels.

On the other hand, USP 2002/0061931, demonstrates that the presence of chloride ion above 20 ppm upto 100 ppm and of gabalactam upto 0.5% in samples of gabapentin obtained from its hydrochloride by the method outlined in U.S. Pat. No. 6,255,526 (for example suspension of the hydrochloride in ethyl acetate stirred with (tri-n-butylamine for 2 hours at 25 deg C. and filtered) have the desired stability.

Another important aspect to be considered while developing a process for the preparation of gabapentin from its hydrochloride is regarding the purity of Gabapentin which is to be used in the pharmaceutical applications/formulations containing it. This aspect, which is a recent development, is concerned with the stringent specifications proposed by the Pharmaceutical Forum. Some of the important specifications stipulated and which are relevant to the present invention, are the following:

| | | |
|---|---|---|
| 1. | Chloride content | NMT 100 ppm |
| 2. | Gabalactam content | less than 0.1% |

-continued

| | | |
|---|---|---|
| 3. | Impurity with RF 0.5 relative to gabapentin | less than 0.2% |
| 4. | Any other individual impurity | less than 0.1% |
| 5. | Total impurities | less than 0.5%, excluding the impurity mentioned in item 3 |

The specifications of individual formulators are even more stringent with limits wherein the limitation of Gabalactam should be less than 0.05% and impurity with RF 0.5 relative to gabalapentin being—less than 0.1%.

Therefore the gabapentin which will be obtained by any process should meet the above stringent requirements as otherwise it will not be useful for pharmaceutical applications. The method at the same time must be capable of affording pure gabapentin conforming to the stringent specifications of the Pharmaceutical Forum mentioned earlier.

Currently Gabapentin is a high selling drug (falling within top ten in the world market) as it can also be used for the treatment of deep neural pain, in addition to its known anti epileptic activity. Understanding clearly from the above described state of the art literature and taking into consideration the stringent pharmaceutical specifications it is felt that if a simple, inexpensive method is developed for the preparation of gabapentin from its salts, especially hydrochloride, avoiding low temperature evaporation of large volumes of solvents such as water or use of tertiary amines which are likely to contaminate the final products, it would lead to a process for preparing Gabapentin in commercial quantities to meet the increasing global demand.

Accordingly we took up research and development work towards development of an improved process for the preparation of gabapentin. Gabapentin so prepared meets the stringent pharmaceutical specifications mentioned earlier Accordingly, the main objective of the present invention is to provide an improved process for the preparation of gabapentin overcoming the above-mentioned difficulties and to produce gabapentin meeting the stringent pharmaceutical specifications.

Another objective of the present invention is to provide an improved process for the preparation of gabapentin, which does not involve the costly ion exchange conversion of gabapentin hydrochloride, making the process simple and economical Yet another objective of the present invention is to provide an improved process for the preparation gabapentin which results in high purity (over 99.5%) gabapentin Still another objective of the present invention is to provide an improved process for the preparation of gabapentin which results in high yield (over 50%)

From the above mentioned prior art literature relating to the preparation of gabapentin it would be observed that an easy and simple method for the liberation of gabapentin from its hydrochloride salt would be to neutralize an aqueous solution of the latter with aqueous alkali or alkali earth hydroxide. This method, surprisingly, has not been attempted or reported in the literature. Such a method has not so far been attempted, perhaps, considering the fact that gabapentin, being an aminoacid, will be water soluble and cannot be precipitated even at the isoelectric point in desirable yields namely of more than 50%.

In the Indian patent No 186285, a process for the preparation of gabapentin has been disclosed which produces a substantially pure gabapentin. The process described is given below:

The process involves isolation of substantially pure 1-(aminomethyl) cyclohexaneacetic acid directly from an aqueous solution of its acid addition salt, The acid addition salt used is an addition product of 1-(aminomethyl)cyclohexaneacetic acid with a mineral acid selected from hydrochloric acid, sulphuric acid, phosphoric acid, nitric acid, or with an organic acid selected from C1 to C12 aliphatic carboxylic acid, C1 to C7 aliphatic sulphonic acid, aryl sulphonic acid and a polycarboxylic acid, comprising addition of a base to an aqueous solution of the 1-(aminomethyl)cyclohexaneacetic acid addition salt to adjust the pH between 6.7 to 8 to precipitate 1-(aminomethyl)cyclohexaneacetic acid, followed by washing the precipitated 1-(aminomethyl)cyclohexaneacetic acid with a water miscible organic solvent, and drying the precipitated 1-(aminomethyl)cyclohexaneacetic acid to obtain substantially pure 1-(aminomethyl)cyclohexaneacetic acid which contains less than 0.2% 2-azaspiro[4,5]decan-3-one.

The base employed in the process is generally an alkali or alkaline earth metal hydroxide or carbonate.

Specific examples of alkali and alkaline earth metal hydroxides and carbonates that may be used include NaOH, KOH, LiOH, CsOH, Mg(OH)$_2$, Ca (OH)$_2$, Ba(OH)$_2$, Li2CO3, Na2CO3, K2CO3, Cs2CO3 or mixtures thereof. The preferred base is an alkali metal hydroxide. More preferably the base is sodium hydroxide.

During the treatment with hydroxide base in the process, the pH is adjusted from an acidic pH to a pH between 6.7 to 8, preferably between 7.2 to 7.8.

The adjustment of pH with hydroxide base is carried out at temperature between 0 to 50 deg C., preferably between 10 to 40 deg C. and more preferably between 15 to 25 deg C. After adjusting the pH the reaction mixture is allowed to stand for sufficient time ranging from 1 to 12 hour for efficient crystallization of 1-(aminomethyl)cyclohexaneacetic acid. The crystallized 1-(aminomethyl) cyclohexaneacetic acid is washed with a water-miscible organic solvent, preferably acetone and dried to obtain substantially pure anhydrous 1-(aminomethyl)cyclohexaneacetic acid.

When we tried to repeat the above-explained process with the help of details given in the experimental section (Example 2) of Indian patent no 186285, we found that gabapentin so prepared was not falling within the pharmaceutical specifications explained above. The gabapentin obtained by the above method was found to be containing un-acceptably large amount namely more than 3% vs less than 100 ppm of chlorides and total impurity levels of more than 1.5% as against 0.5% required by pharmacopia Therefore we observed that the above-mentioned process seems to be not suitable for the preparation of gabapentin satisfying the stringent pharmaceutical specifications explained above.

Systematic and sustained investigations made by us with (i) various volumes of water for dissolving gabapentin hydrochloride, (ii) various strengths of neutralizing alkali, (iii) various temperatures of neutralization, (iv) various aging time of the precipitate, (v) various compositions of liquids for washing the filter cake and (vi) crystallization procedures resulted in our finding that an improved process for the preparation of gabapentin can be developed Gabapentin prepared by the process developed according to the process of the present invention, meets the above mentioned stringent pharmaceutical stipulations and also results in good yields (say 40 to 60%) with total impurity levels less than 0.5% and chloride contents less than 100 ppm as required by pharmacopia Thus, according to the present invention, it is possible to prepare gabapentin, which will have the purity of 99.5%, yield of 40 to 60% and finally meeting all the above-mentioned stringent specifications for its use in the pharmaceutical field.

In other words we could achieve a result, which could not have been anticipated by the prior art knowledge.

Accordingly the present invention provides an improved process for the preparation of gabapentin of the formula 1

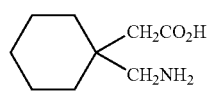

1 which comprises (i) preparing an aqueous solution of Gabapentin hydrochloride in water in the ratio of one part by weight of the former to 0.5 to 3 parts by weight of the later, (ii) preparing an aqueous solution of an alkali metal base in a concentration in the range of 40-50% w/w (iii) adding 0.08 to 0.3 parts by weight of the solution obtained in step (ii) to 1.5 to 4 parts by weight of the solution obtained in step (i) at a temperature in the range of 0 to 20 degree C.

(iv) heating the resulting solution gradually to a temperature in the range of 50-90 degree C.

(v) gradually cooling the resulting solution to a temperature in the range of 0 to 15 degree C. to obtain a precipitate, (vi) aging the precipitate for a period in the range of 0.5 hrs to 8 hrs at a temperature in the range of 0 to 15 degree C.

(vii) Separating the precipitate from the mother liquor by conventional methods and (viii) recrystallising the precipitate from a mixture of IPA, Methanol & water to get Gabapentin of over 99.5% purity and a mother liquor In a preferred embodiment of the invention the various steps may be performed as follows The amount of gabapentin hydrochloride and water used in step (i) may preferably be 0.5 to 2.5 parts of water to 1 part of the Gabapentin hydrochloride and more preferably 1.5 to 2.5 parts of the water The alkali used in step (ii) may preferably be sodium hydroxide or potassium hydroxide, more preferably sodium hydroxide. The solution used may be in a concentration in the range of 40-50% w/w more preferably in the concentration in the range of 45-50% w/w in water.

The temperature employed in step (iii) may be preferably 10-20 deg C. and more preferably 10-15 deg C.

The temperature employed in step (iv) used may preferably be 50-75 deg C. and more preferably 60-70 deg C. The gradual heating may be effected during a period of 1 to 3 hrs The temperature employed in step (v) may be preferably 5-15 C. deg and most preferably 5-10 deg C. The said cooling may be effected gradually during a period of 1.5 to 3 hrs The time employed for aging the precipitate in step (vi) may preferably be between 0.5 to 3 hrs and more preferably 0.5 to 1 hr.

The method of separation used in step (vii) may preferably be filtration, more preferably centrifugation].

In another preferred embodiment of the invention the solution of the gabapentin hydrochloride prepared is treated with charcoal and filtered through hyflobed to de-colourise the solution before basification.

The process of the present invention while avoiding the usage of liquid resins, aromatic amines and high-energy requirements, gives cycloalkane amino methyl acetic acids in pharmaceutically purer form. The process gives 1-aminomethyl-cyclohexane acetic acid in which the sum of all impurities determined by the pharmacopoeia method as described in USP-NF is not more than 0.5% and no unknown impurity more than 0.1%. The toxic gabalactam is also controlled to a limit of less than 0.1%. The chloride contents are substantially lower than (between 50-60 ppm) the prescribed pharmacoepial limits, (less than 100 ppm) while not compromising on the final yield of the material.

It is to be noted that the process defined above can be extended to other 1-aminomethylcycloalkane-1-acetic acids of the general formula 2

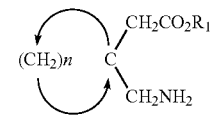

2 where 'n' represents an integer from 4-6.

This can be done from precursor lactams of the general formula 4,

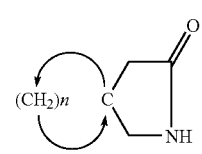

4 where n has the meaning given above, through the intermediacy of the hydrochloride salts which can be neutralized with alkali or alkali earth hydroxide solutions.

The process of the present invention has been made more economical by utilizing the mother liquors resulting from the steps (vii) & (viii) of the process to prepare Gabalactam of the formula 3.

Accordingly the invention also provides a novel improved process for the preparation of Gabalactam of the formula 3 which comprises treating the mother liquors obtained in steps (vii) & (viii) of the above mentioned process with aq.sodium hydroxide in a concentration in the range of 5 to 20% at a temperature in the range of 80 to 100 degree C., recovering the gabalactam by extraction with organic solvents.

In a preferred embodiment the concentration of sodium hydroxide may range from 10- to 20%, the temperature may range from 80 to 85 deg C.

In yet another embodiment the recovery of gabalactam can be effected by extracting the reaction mixture with solvents such as toluene, ethylene dichloride, methylene dichloride or hexane preferably toluene.

The gabalactam, which is so prepared, can be used for the preparation of Gabapentin Hydrochloride, which is the starting material for the process preparation of gabapentin as explained above.

The details of the invention are given in the Examples given below which are provided only for illustrative purposes and therefore should not be construed to limit the scope of the invention

EXAMPLE 1

Gabapentin hydrochloride (267 g); is dissolved in chloride free demineralized water (375 ml) at 50 degrees. The solution is treated with charcoal at the same temperature and filtered through a bed of hyflo. The bed is washed with demineralized water (150 ml). The filtrate is cooled to 10 deg and neutralized with sodium lye (110 g of 50% w/w sodium hydroxide solution) with the temperature kept strictly below 15 degrees. The neutralized mixture is heated to 70-75 degrees over a period of 3 hours to get a clear solution, then cooled to 5-10 degrees over a period of 4 hours and kept at that temperature range for 1 hr and filtered (mother liquor A). The product is suck dried thoroughly to give moist gabapentin (about 195 g) having water content of 14%. This is dissolved in a mixture of methanol (570 ml) and water (60 ml) at about 70 degrees. The solution is treated with activated charcoal (5 g) and filtered through a bed of hyflo. The bed is washed with a mixture of methanol (80 ml) and water (16 ml). To the combined filtrates is added isopropanol (815 ml). The mixture is cooled to 0-5 degrees and maintained for 1 hr, when pure white gabapentin crystallizes out, the mixture is centrifuged; the product is spin-dried for 45 min (mother liquor B) and dried to yield gabapentin (125 g) with 1. Chloride 40 ppm, 2. Gabalactam, 0.01%, 3. Impurity with RF 0.5 relative to gabapentin NIL 4. Any other individual impurity less than 0.1% 5. Total impurities 0.032%

EXAMPLE 2

Gabapentin.hydrochloride (100 g) is dissolved in chloride free demineralised water (290 ml) at 50-60 deg. The solution is treated with charcoal at the same temperature and filtered through a bed of hyflo. The bed is washed with demineralised water (10 ml). The filtrate is cooled to 0-10 deg C. and neutralized with 43 g of around 45% w/w sodium hydroxide solution at the same temperature and maintained for half an hour. Then the reaction mixture is heated to 60-65 deg C. over a period of 2 hours and then cooled to 0-5 deg C. over a period of 3 hours, maintained at 0-5 deg for 1 hr. The precipitated gabapentin is filtered, the product suck dried to give moist gabapentin (60 g), having water content of 15%. This is dissolved in a mixture of methanol (192 ml) and water (11 ml) at about 70 degrees. The solution is treated with activated charcoal (1 g) and filtered through a bed of hyflo. The bed is washed with a mixture of methanol (27 ml) and water (3 ml). To the combined filtrates is added isopropanol (275 ml). The mixture is cooled to 0-5 degrees and maintained for 1 hr. when pure white gabapentin crystallizes out the mixture is centrifuged; the product is spin-dried for 45 min (mother liquor B) and dried to yield gabapentin (35 g) with 1. Chloride 50 ppm, 2. Gabalactam 0.03%, 3. Impurity with RF 0.5 relative to gabapentin 0.05%, 4. Any other individual impurity not more than 0.1% 5. Total impurities 0.3% (excluding 3)

EXAMPLE 3

Gabapentin.hydrochloride (100 g) is dissolved in chloride free demineralised water (250 ml) at 50-60 deg. The solution is treated with charcoal at the same temperature and filtered through a bed of hyflo. The filtrate is cooled to around 15 deg and neutralized with 44 g of 40% w/w sodium hydroxide solution at the same temperature and maintained for half an hour. Then the reaction mixture is heated to 65-70 deg over a period of one and half hours and then cooled to 5-10 deg over a period of 2 hrs, maintained at 5-10 deg for 2 hr. The precipitated gabapentin is filtered, the product suck dried to give moist gabapentin (61 g) having water content of 14%. This is dissolved in a mixture of methanol (145 ml) and water (23 ml) at about 70 degrees. The solution is treated with activated charcoal (1 g) and filtered through a bed of hyflo. The bed is washed with a mixture of methanol (20 ml) and water (6 ml). To the combined filtrates is added isopropanol (174 ml). The mixture is cooled to 0-5 degrees and maintained for 1 hr, when pure white gabapentin crystallizes out, the mixture is centrifuged; the product is spin-dried for 45 min (mother liquor B) and dried to yield gabapentin (38 g) with 1. Chloride 60 ppm, 2. Gabalactam 0.02%, 3. Impurity with RF 0.5 relative to gabapentin 0.07%, 4. Any other individual impurity not more than 0.1% 5. Total impurities less than 0.4%, excluding 3

EXAMPLE 4

Gabapentin.hydrochloride (100 g) is dissolved in chloride free deminaralized water (150 ml) at 50-60 deg. The solution is treated with charcoal at the same temperature and filtered through a bed of hyflo. The filtrate is cooled to 0-10 deg and neutralized with 43 g of 45% w/w sodium hydroxide solution at around 1.5 deg and maintained for half an hour. Then the reaction mixture is heated to 70-80 deg over a period of 3 hrs and then cooled to around 15 deg over a period of 1.5 hrs, maintained at 15 deg for half an hour. The precipitated gabapentin is filtered, the product suck dried to give moist gabapentin (70 g) having water content of 12%. This is dissolved in a mixture of methanol (240 ml) and water (30 ml) at about 70 degrees. The solution is treated with activated charcoal (1 g) and filtered through a bed of hyflo. The bed is washed with a mixture of methanol (33 ml) and water (8 ml). To the combined filtrates is added isopropanol (360 ml). The mixture is cooled to 0-5 degrees and maintained for 1 hr, when pure white gabapentin crystallizes out, the mixture is centrifuged; the product is spin-dried for 45 min (mother liquor B) and dried to yield gabapentin (41 g), 1. Chloride 90 ppm, 2. Gabalactam 0.04% 3. Impurity with RF 0.5 relative to gabapentin 0.09% 4. Any other individual impurity not more than, 0.1%, 5. Total impurities 0.4%, excluding 3

EXAMPLE 5

Gabapentin.hydrochloride (100 g) is dissolved in chloride free demineralised water (200 ml) at 50-60 deg. The solution is treated with charcoal at the same temperature and filtered through a bed of hyflo. The filtrate is cooled to 0-10 deg and neutralized with 45 g of 50% w/w sodium hydroxide solution at the same temperature and maintained for half an hour. Then the reaction mixture is heated to 65-70 deg over a period of 2 hrs and then cooled to 5-10 deg over 2.5 hrs, maintained at 5-10 deg for 4 hr. The precipitated gabapentin is filtered, the product suck dried to give moist gabapentin (65 g) having water content of 17%. This is dissolved in a mixture of methanol (174 ml) and water (20 ml) at about 70 degrees. The solution is treated with activated charcoal (1 g) and filtered through a bed of hyflo. The bed is washed with a mixture of methanol (25 ml) and water (5 ml). To the combined filtrates is added isopropanol (116 ml). The mixture is cooled to 0-5 degrees and maintained for 1 hr, when pure white gabapentin crystallizes out, the mixture is centrifuged; the product is spin-dried for 45 min (mother liquor B) and dried to yield gabapentin (39 g), 1. Chloride 50 ppm, 2. Gabalactam 0:04%, 3. Impurity with RF 0.5 relative to gabapentin NIL, 4. Any other individual impurity not more than 0.1%, 5. Total impurities 0.3%, excluding 3

EXAMPLE 6

Gabapentin.hydrochloride (100 g) is dissolved in chloride free demineralised water (180 ml) at 50-60 deg. The solution is treated with charcoal at the same temperature and filtered through a bed of hyflo. The filtrate is cooled to around 10 deg and neutralized with 45 g of 50% w/w sodium hydroxide solution at the same temperature and maintained for half an hour. Then the reaction mixture is heated to 65-70 deg over a period of 2.5 hrs and then cooled to around 10 deg over a period of 2.5 hrs, maintained at around 10 deg for 4 hr. The precipitated gabapentin is filtered, the product suck dried to give moist gabapentin (63 g) having water content of 15%. This is dissolved in a mixture of methanol (360 ml) and water (21 ml) at about 70 degrees. The solution is treated with activated charcoal (1 g) and filtered through a bed of hyflo. The bed is washed with a mixture of methanol (50 ml) and water (5.5 ml). To the combined filtrates is added isopropanol (360 ml). The mixture is cooled to 0-5 degrees and maintained for 1 hr. when pure white gabapentin crystallizes out the mixture is centrifuged; the product is spin-dried for 45 min (mother liquor B) and dried to yield gabapentin (40 g), 1. Chloride 60 ppm, 2. Gabalactam 0.04%. 3. Impurity with RF 0.5 relative to gabapentin 0.08%, 4. Any other individual impurity not more than 0.1% 5. Total impurities 0.28% excluding 3

EXAMPLE 7

Gabapentin.hydrochloride (300 g) is dissolved in chloride free demineralised water (525 ml) at 50-60 deg. The solution is treated with charcoal at the same temperature and filtered through a bed of hyflo. The filtrate is cooled to around 10-15 deg and neutralized with 120 g of 43% w/w sodium hydroxide solution at the same temperature and maintained for half an hour. Then the reaction mixture is heated to 70-75 deg over a period of 3 hrs and then cooled to 5-15 deg over a period of 2.5 hrs, maintained at 5-15 deg for 6 hr. The precipitated gabapentin is filtered, the product suck dried to give moist gabapentin (210 g), having water content of 16%. This is dissolved in a mixture of methanol (625 ml) and water (50 ml) at about 70 degrees. The solution is treated with activated charcoal (3 g) and filtered through a bed of hyflo. The bed is washed with a mixture of methanol (86 ml) and water (13 ml). To the combined filtrates is added isopropanol (500 ml). The mixture is cooled to 0-5 degrees and maintained for 1 hr, when pure white gabapentin crystallizes out. The mixture is centrifuged; the product is spin-dried for 45 min (mother liquor B) and dried to yield gabapentin (120 g), with 1. Chloride 70 ppm, 2. Gabalactam 0.045%, 3. Impurity with RF 0.5 relative to gabapentin 0.08%, 4. Any other individual impurity not more than 0.1% 5. Total impurities 0.35%, excluding 3

EXAMPLE 8

Gabapentin.hydrochloride (100 g) is dissolved in chloride free demineralised water (120 ml) at 50-60 deg. The solution is treated with charcoal at the same temperature and filtered through a bed of hyflo. The filtrate is cooled to around 10-15 deg and neutralized with 45 g of 40% w/w sodium hydroxide solution at the same temperature and maintained for half an hour. Then the reaction mixture is heated to 70-80 deg over a period of 1 hr and then cooled to around 15 deg over a period of 2 hrs, maintained at around 15 deg for 8 hrs. The precipitated gabapentin is filtered, the product suck dried to give moist gabapentin (72 g) having water content of 18%. This is dissolved in a mixture of methanol (260 ml) and water (36 ml) at about 70 degrees. The solution is treated with activated charcoal (1 g) and filtered through a bed of hyflo. The bed is washed with a mixture of methanol (3.6 ml) and water (9 ml). To the combined filtrates is added isopropanol (260 ml). The mixture is cooled to 0-5 degrees and maintained for 1 hr, when pure white gabapentin crystallizes out, the mixture is centrifuged; the product is spin-dried for 45 min (mother liquor B) and dried to yield gabapentin (41 g) 1. Chloride 90 ppm, 2. Gabalactam 0.04%, 3. Impurity with RF 0.5 relative to gabapentin 0.085%, 4. Any other individual impurity not more than 0.1% 5. Total impurities 0.4% excluding 3

EXAMPLE 9

Gabapentin.hydrochloride (100 g) is dissolved in chloride free demineralised water (110 ml) at 50-60 deg. The solution is treated with charcoal at the same temperature and filtered through a bed of hyflo. The filtrate is cooled to 15-20 deg and neutralized with 41 g of 40% w/w sodium hydroxide solution at the same temperature and maintained for half an hour. Then the reaction mixture is heated to around 80 deg over a period of 2 hrs and then cooled to around 15 deg over a period of 2 hrs, maintained at 5-10 deg for 3 hr. The precipitated gabapentin is filtered, the product suck dried to give moist gabapentin (74 g) having water content of 16%. This is dissolved in a mixture of methanol (370 ml) and water (45 ml) at about 70 degrees. The solution is treated with activated charcoal (1 g) and filtered through a bed of hyflo. The bed is washed with a mixture of methanol (52 ml) and water (12 ml). To the combined filtrates is added isopropanol (370 ml). The mixture is cooled to 0-5 degrees and maintained for 1 hr, when pure white gabapentin crystallizes out, the mixture is centrifuged; the product is spin-dried for 45 min (mother liquor B) and dried to yield gabapentin. (46 g) with 1. Chloride 90 ppm, 2. Gabalactam 0.045%, 3. Impurity with RF 0.5 relative to gabapentin 0.09%, 4. Any other individual impurity not more than 0.1%, 5. Total impurities 0.4%, excluding 3

EXAMPLE 10

Gabapentin.hydrochloride (200 g) is dissolved in chloride free demineralised water (150 ml) at 50-60 deg. The solution is treated with charcoal at the same temperature and filtered through a bed of hyflo. The filtrate is cooled to around 20 deg and neutralized with 84 g of 50% w/w sodium hydroxide solution at the same temperature and maintained for half an hour. Then the reaction mixture is heated to 80-90 deg over a period of 2.5 hrs and then cooled to around 15 deg over a period of 2 hrs, maintained at 15 deg for half an hour. The precipitated gabapentin is filtered, the product suck dried to give moist gabapentin (135 g) having water content of 17%. This is dissolved in a mixture of methanol (450 ml) and water (105 ml) at about 70 degrees. The solution is treated with activated charcoal (2 g) and filtered through a bed of hyflo. The bed is washed with a mixture of methanol (63 ml) and water (27 ml). To the combined filtrates is added isopropanol (600 ml). The mixture is cooled to 0-5 degrees and maintained for 1 hr, when pure white gabapentin crystallizes out, the mixture is centrifuged; the product is spin-dried for 45 min (mother liquor B) and dried to yield gabapentin (79 g) with 1. Chloride 95 ppm, 2. Gabalactam 0.04%, 3. Impurity with RF 0.5 relative to gabapentin 0.095%, 4. Any other individual impurity not more than 0.1% 5. Total impurities 0.45%, excluding 3

Recovery of Gaba Lactam from Mother Liquors

Mother liquor B obtained from the Example 1 is concentrated under vacuum to a volume of 150 ml at less than 85 degrees and mother liquor A obtained from the Example 1 is added to the concentrated mass. The mixture is treated with 10% sodium hydroxide (100 ml) and heated to 80-85 degrees for 2 hr. It is extracted at about 50 degrees with toluene (200 ml) and the toluene layer is separated. The aqueous layer is again heated at 80-85 degrees for 2 hr and extracted with a second lot of toluene (200 ml). The combined toluene layers are treated with charcoal (2 g) at room temperature and filtered through a bed of hyflo. The filtrate is shaken with water (2×50 ml). The toluene solution is then evaporated to dryness in vacuo to give gabalactam (40 g). The recovered lactam is then converted to gabapentin hydrochloride by the known methods and gabapentin isolated from the same as per the process described above. The recovery of gabapentin from the hydrochloride thus works out to be 77% on recycling.

The process can be scaled up to a charge of 400 kg of gabapentin hydrochloride to afford gabapentin in 75-80% yield after recycling the mother liquors as described herein.

ADVANTAGES OF THE INVENTION (i) The process is simple and economical because it uses only sodium hydroxide and does not require concentrations of high volumes of solvents at reduced pressure.
(ii) The yield is as high as 75% upon recycling.
(iii) The purity of gabapentin produced is as high as 99.5% by HPLC method.
(iv) Gabapentin obtained, meets all the stringent requirements for its use in pharmaceutical field
(v) The by product resulting from the process namely the mother liquors can be utilised to prepare gabalactam which can in turn be utilized to prepare gabapentin hydrochloride, the starting material for the process of this invention thereby making the process more economical.
(vi) The process does not use any ion exchange resin

We claim:

1. An acetone-free process for the preparation of Gabapentin of the following formula

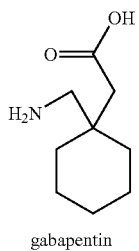

gabapentin which consists essentially of:
(i) preparing an ethanol-free aqueous solution of Gabapentin hydrochloride in water in a ratio of one part by weight of the Gabapentin hydrochloride to 0.5 to 3 parts by weight of the water;
(ii) preparing an aqueous solution of an alkali metal base in a concentration in the range of 40-50% w/w;
(iii) adding 0.08 to 0.3 parts by weight of the solution obtained in step (ii) to 1.5 to 4 parts by weight of the solution obtained in step (i) at a temperature in the range of 0 to 20 degree C. to form a resulting solution;
(iv) heating the resulting solution gradually to a temperature in the range of 60-90 degree C.;
(v) gradually cooling the resulting solution to a temperature in the range of 0 to 15 degree C. to obtain a precipitate;
(vi) aging the precipitate for a period of time in the range of 0.5 hrs to 8 hrs at a temperature in the range of 0 to 15 degree C.;
(vii) separating the precipitate from its mother liquor; and
(viii) recrystallizing the precipitate from a mixture of isopropyl alcohol, methanol and water in a ratio ranging from 4.54-19.64:3.88-15.64:1 (v/v), wherein the ratio of isopropyl alcohol to methanol is in the range from 0.58:1 to 1.32:1 (v/v), to get Gabapentin of over 99.5% purity and another mother liquor, wherein Gabapentin has a chloride content of 100 ppm or less.

2. The process as claimed in claim 1, wherein the amount of the Gabapentin hydrochloride and the water in step (i) is in the ratio of 0.5 to 2.5 parts of water to 1 part of the Gabapentin hydrochloride.

3. The process as claimed in claim 1, wherein the alkali metal base in step (ii) is sodium hydroxide, or potassium hydroxide.

4. The process as claimed in claim 1, wherein the solution of the alkali metal base in step (ii) is in a concentration in the range of 45-50% w/w in water.

5. The process as claimed in claim 1, wherein the temperature employed in step (iii) is 10 to 20 deg C.

6. The process as claimed in claim 1, wherein the temperature in step (iv) is in the range of 60 to 75 deg C.

7. The process as claimed in claim 1, wherein the temperature in step (v) is in the range of 5 to 15 degree C.

8. The process as claimed in claim 1, wherein the time for aging the precipitate in step (vi) is between 0.5 to 3 hrs.

9. The process as claimed in claim 1, wherein the separation of the precipitate in step (vii) is effected by filtration or centrifugation.

10. An acetone-free process for the preparation of Gabalactam of the following formula

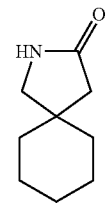

which consists essentially of:
(i) preparing an ethanol-free aqueous solution of Gabapentin hydrochloride in water in a ratio of one part by weight of the Gabapentin hydrochloride to 0.5 to 3 parts by weight of the water;
(ii) preparing an aqueous solution of an alkali metal base in a concentration in the range of 40-50% w/w;
(iii) adding 0.08 to 0.3 parts by weight of the solution obtained in step (ii) to 1.5 to 4 parts by weight of the solution obtained in step (i) at a temperature in the range of 0 to 20 degree C. to form a resulting solution;

(iv) heating the resulting solution gradually to a temperature in the range of 60-90 degree C.;
(v) gradually cooling the resulting solution to a temperature in the range of 0 to 15 degree C. to obtain a precipitate;
(vi) aging the precipitate for a period of time in the range of 0.5 hrs to 8 hrs at a temperature in the range of 0 to 15 degree C.;
(vii) separating the precipitate from its mother liquor;
(viii) recrystallizing the precipitate from a mixture of isopropyl alcohol, methanol and water in a ratio ranging from 4.54-19.64:3.88-15.64:1 (v/v), wherein the ratio of isopropyl alcohol to methanol is in the range from 0.58:1 to 1.32:1 (v/v), to get Gabapentin of over 99.5% purity, wherein the Gabapentin has a chloride content of 100 ppm or less, and another mother liquor;
(ix) treating the mother liquors from steps (vii) & (viii) with an aqueous solution of sodium hydroxide in a concentration in the range of 5 to 20% at a temperature in the range of 80 to 100 degree C.; and
(x) recovering Gabalactam from step (ix) by extraction with organic solvents.

11. The process as claimed in claim 10, wherein in step (ix), the concentration of the solution of sodium hydroxide ranges from 10 to 20%, and the temperature ranges from 80 to 85 degree C.

12. The process as claimed in claim 10, wherein in step (x), the organic solvents are selected from the group consisting of toluene, ethylene dichloride, methylene dichloride and hexane.

13. The process as claimed in claim 1, wherein the chloride content is 40 to 95 ppm.

14. The process as claimed in claim 1, wherein the chloride content is 40 to 90 ppm.

15. The process as claimed in claim 1, wherein the chloride content is 40 to 70 ppm.

16. The process as claimed in claim 1, wherein the chloride content is 40 to 60 ppm.

17. The process as claimed in claim 1, wherein the chloride content is 40 to 50 ppm.

18. An acetone-free process for the preparation of Gabapentin of the following formula

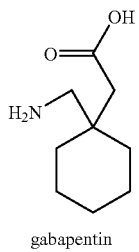

gabapentin which consists essentially of:
(i) providing an ethanol-free aqueous solution of Gabapentin hydrochloride having a ratio of parts by weight of Gabapentin hydrochloride to parts by weight of water from 0.5 to 3;
(ii) adding 0.08 to 0.3 parts by weight of an aqueous alkali metal base solution at a concentration from 40 to 50% w/w to 1.5 to 4 parts by weight of the aqueous solution of the Gabapentin hydrochloride to form a resulting solution at a temperature in the range from 0 to 20 degree C.;
(iii) heating the resulting solution gradually to a temperature from 60 to 90 degree C.;
(iv) gradually cooling the resulting solution gradually to a temperature from 0 to 15 degree C. to obtain a precipitate;
(v) aging the precipitate in the solution at the temperature from 0 to 15 degree C. for a time from 0.5 hrs to 8 hrs;
(vi) separating the precipitate from its mother liquor; and
(vii) recrystallizing the precipitate from a solvent mixture containing isopropyl alcohol, methanol and water in a ratio ranging from 4.54-19.64:3.88-15.64:1 (v/v), wherein the ratio of isopropyl alcohol to methanol is in the range from 0.58:1 to 1.32:1 (v/v), to obtain Gabapentin of at least 99.5% purity and having a chloride content of 100 ppm or less, and a Gabalactam content of 0.05% or less,
wherein the process excludes an ion exchange conversion of Gabapentin hydrochloride, and
wherein the Gabapentin has a chloride content of 100 ppm or less.

19. The process of claim 18, wherein the chloride content is from 40 to 50 ppm and the Gabalactam content is from 0.01 to 0.045%.

20. An acetone-free process for the preparation of Gabapentin of the following formula

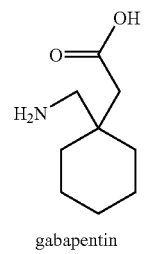

gabapentin which consists essentially of:
(i) preparing an ethanol-free aqueous solution of Gabapentin hydrochloride in water in a ratio of one part by weight of the Gabapentin hydrochloride to 0.5 to 3 parts by weight of the water;
(ii) preparing an aqueous solution of an alkali metal base in a concentration in the range of 40-50% w/w;
(iii) adding 0.08 to 0.3 parts by weight of the solution obtained in step (ii) to 1.5 to 4 parts by weight of the solution obtained in step (i) at a temperature in the range of 0 to 20 degree C. to form a resulting solution;
(iv) heating the resulting solution gradually to a temperature in the range of 60-90 degree C.;
(v) gradually cooling the resulting solution to a temperature in the range of 0 to 15 degree C. to obtain a precipitate;
(vi) aging the precipitate for a period of time in the range of 0.5 hrs to 8 hrs at a temperature in the range of 0 to 15 degree C.;
(vii) separating the precipitate from its mother liquor; and
(viii) recrystallizing the precipitate from a mixture of isopropyl alcohol, methanol and water in a ratio ranging from 4.54-19.64:3.88-15.64:1 (v/v), wherein the ratio of isopropyl alcohol to methanol is in the range from 0.58:1 to 1.32:1 (v/v), to obtain Gabapentin of over 99.5% purity and another mother liquor, wherein the Gabapentin has a chloride content of 100 ppm or less and
wherein the process produces a yield of Gabapentin that is over 50%.

21. An acetone-free process for the preparation of Gabalactam of the following formula:

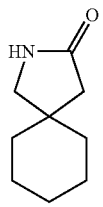

which consists essentially of:
(i) preparing an ethanol-free aqueous solution of Gabapentin hydrochloride in water in a ratio of one part by weight of the Gabapentin hydrochloride to 0.5 to 3 parts by weight of the water;
(ii) preparing an aqueous solution of an alkali metal base in a concentration in the range of 40-50% w/w;
(iii) adding 0.08 to 0.3 parts by weight of the solution obtained in step (ii) to 1.5 to 4 parts by weight of the solution obtained in step (i) at a temperature in the range of 0 to 20 degree C. to form a resulting solution
(iv) heating the resulting solution gradually to a temperature in the range of 60-90 degree C.;
(v) gradually cooling the resulting solution to a temperature in the range of 0 to 15 degree C. to obtain a precipitate;
(vi) aging the precipitate for a period of time in the range of 0.5 hrs to 8 hrs at a temperature in the range of 0 to 15 degree C.;
(vii) separating the precipitate from its mother liquor;
(viii) recrystallizing the precipitate from a mixture of isopropyl alcohol, methanol and water in a ratio ranging from 4.54-19.64:3.88-15.64:1 (v/v), wherein the ratio of isopropyl alcohol to methanol is in the range from 0.58:1 to 1.32:1 (v/v), to obtain Gabapentin of over 99.5% purity, wherein the Gabapentin is produced in a yield of over 50% and has a chloride content of 100 ppm or less, and another mother liquor;
(ix) treating the mother liquors from steps (vii) & (viii) with an aqueous solution of sodium hydroxide in a concentration in the range of 5 to 20% at a temperature in the range of 80 to 100 degree C.; and
(x) recovering Gabalactam from step (ix) by extraction with organic solvents.

22. An acetone-free process for the preparation of Gabapentin of the following formula:

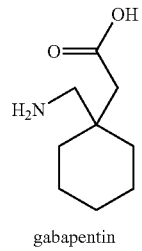

gabapentin which consists essentially of:
(i) providing an ethanol-free aqueous solution of Gabapentin hydrochloride having a ratio of parts by weight of Gabapentin hydrochloride to parts by weight of water from 0.5 to 3;
(ii) adding 0.08 to 0.3 parts by weight of an aqueous alkali metal base solution at a concentration from 40 to 50% w/w to 1.5 to 4 parts by weight of the aqueous solution of the Gabapentin hydrochloride to form a resulting solution at a temperature in the range from 0 to 20 degree C.;
(iii) heating the resulting solution gradually to a temperature from 60 to 90 degree C.;
(iv) gradually cooling the resulting solution to a temperature from 0 to 15 degree C. to obtain a precipitate;
(v) maintaining the precipitate in the solution at the temperature from 0 to 15 degree C. for a time from 0.5 hrs to 8 hrs;
(vii) separating the precipitate from its mother liquor; and
(viii) recrystallizing the precipitate from a solvent mixture containing isopropyl alcohol, methanol and water in a ratio ranging from 4.54-19.64:3.88-15.64:1 (v/v), wherein the ratio of isopropyl alcohol to methanol is in the range from 0.58:1 to 1.32:1 (v/v), to obtain Gabapentin of at least 99.5% purity and having a chloride content of 100 ppm or less, and a Gabalactam content of 0.05% or less,
wherein the process excludes an ion exchange conversion of Gabapentin hydrochloride, and wherein the Gabapentin has a chloride content of 100 ppm or less, and further wherein the process produces Gabapentin in a yield of over 50%.

* * * * *